United States Patent
McCloskey

(10) Patent No.: US 11,648,380 B2
(45) Date of Patent: May 16, 2023

(54) DEVICE FOR TREATMENT OF A BODY CANAL AND ADJACENT SURFACES

(71) Applicant: Jenny Colleen McCloskey, Mount Lawley (AU)

(72) Inventor: Jenny Colleen McCloskey, Mount Lawley (AU)

( * ) Notice: Subject to any disclaimer, the term of this patent is extended or adjusted under 35 U.S.C. 154(b) by 136 days.

(21) Appl. No.: 16/770,002

(22) PCT Filed: Dec. 5, 2018

(86) PCT No.: PCT/AU2018/051305
§ 371 (c)(1),
(2) Date: Jun. 4, 2020

(87) PCT Pub. No.: WO2019/109144
PCT Pub. Date: Jun. 13, 2019

(65) Prior Publication Data
US 2020/0384249 A1   Dec. 10, 2020

(30) Foreign Application Priority Data

Dec. 5, 2017 (AU) .............................. 2017904884

(51) Int. Cl.
*A61M 31/00* (2006.01)
*A61M 25/10* (2013.01)

(52) U.S. Cl.
CPC ............ *A61M 31/00* (2013.01); *A61M 25/10* (2013.01); *A61M 2202/206* (2013.01);
(Continued)

(58) Field of Classification Search
CPC .......... A61M 31/00; A61M 2210/1433; A61M 25/0668; A61B 17/42
See application file for complete search history.

(56) References Cited

U.S. PATENT DOCUMENTS

| 694,971 A | 3/1902 | Kistler |
| 1,383,502 A | 7/1921 | Vultee |

(Continued)

FOREIGN PATENT DOCUMENTS

| CA | 1313803 C | 2/1993 |
| EP | 0088714 A1 | 9/1983 |

(Continued)

OTHER PUBLICATIONS

Sokal, et al, "Inactivation of papillomavirus by low concentrations of povidone-iodine", Sexually Transmitted Diseases vol. 22, No. 1 (Jan.-Feb. 1995) 22-24.

(Continued)

*Primary Examiner* — Deanna K Hall
(74) *Attorney, Agent, or Firm* — Resonance IP Law, PC

(57) ABSTRACT

A device (10, 210) for treatment of a canal associated with an orifice includes a flexible stem portion (20, 220) adapted for insertion along the canal and having an expandable member (24, 224) carried by the stem portion (20, 220) at or adjacent the distal end. The expandable member (24, 224) is for occlusion of an inner end region of the canal. A cap (40, 240, 340) mounted on the stem portion (20, 220), configured as a receptacle (42, 242), to close an outer end of the canal and to accommodate the surface(s) about the outer end of the canal. The cap (40, 240) thereby de-fines with the expandable member (24, 224), a treatment zone, wherein the receptacle (42, 242) is adapted to receive and store treatment fluid for contact with the surface(s) about the outer end of the canal.

24 Claims, 13 Drawing Sheets

(52) U.S. Cl.
CPC . *A61M 2210/1067* (2013.01); *A61M 2210/14* (2013.01); *A61M 2250/00* (2013.01)

(56) References Cited

U.S. PATENT DOCUMENTS

| | | | |
|---|---|---|---|
| 1,737,488 A | 11/1929 | Zohlen | |
| 2,017,334 A | 10/1935 | Edward | |
| 2,085,644 A | 6/1937 | Ferciot | |
| 2,126,257 A | 8/1938 | Hird | |
| 2,494,393 A | 1/1950 | Lamson | |
| 2,687,131 A | 8/1954 | Raiche | |
| 2,764,975 A | 10/1956 | Greenberg | |
| 3,509,884 A | 5/1970 | Bell | |
| 3,841,304 A | 10/1974 | Jones | |
| 3,894,539 A | 7/1975 | Tallent | |
| 3,900,033 A | 8/1975 | Leininger et al. | |
| 3,916,897 A | 11/1975 | Elmore et al. | |
| 4,337,775 A | 7/1982 | Cook et al. | |
| 4,516,578 A | 5/1985 | Shuffield | |
| 4,692,158 A | 9/1987 | Bloxom, Jr. | |
| 4,976,692 A | 12/1990 | Atad | |
| 5,035,883 A | 7/1991 | Witkin | |
| 5,259,836 A | 11/1993 | Thurmond et al. | |
| 5,312,343 A | 5/1994 | Krog et al. | |
| 5,364,375 A | 11/1994 | Swor | |
| 5,372,584 A | 12/1994 | Zink et al. | |
| 5,451,232 A | 9/1995 | Rhinehart et al. | |
| 5,476,095 A | 12/1995 | Schnall et al. | |
| 5,509,427 A | 4/1996 | Simon et al. | |
| 5,530,076 A | 6/1996 | Eguchi et al. | |
| 5,536,243 A | 7/1996 | Jeyendran | |
| 5,613,950 A | 3/1997 | Yoon | |
| 5,769,091 A | 6/1998 | Simon et al. | |
| 5,906,575 A | 5/1999 | Conway et al. | |
| 5,924,423 A | 7/1999 | Majlessi | |
| 5,928,249 A | 7/1999 | Saadat et al. | |
| 5,957,920 A | 9/1999 | Baker | |
| 6,077,257 A | 6/2000 | Edwards et al. | |
| 6,139,538 A * | 10/2000 | Houghton | A61N 1/0524 604/21 |
| 6,409,723 B1 | 6/2002 | Edwards | |
| 6,419,673 B1 | 7/2002 | Edwards et al. | |
| 6,425,853 B1 | 7/2002 | Edwards | |
| 6,470,219 B1 | 10/2002 | Edwards et al. | |
| 6,494,879 B2 | 12/2002 | Lennox et al. | |
| 6,716,252 B2 | 4/2004 | Lazarovitz et al. | |
| 6,939,336 B2 | 9/2005 | Silfver | |
| 7,022,103 B2 | 4/2006 | Cappiello et al. | |
| 7,141,036 B2 | 11/2006 | Berman et al. | |
| 7,291,129 B2 | 11/2007 | Li et al. | |
| 8,016,816 B2 | 9/2011 | Gregory | |
| 8,105,335 B1 | 1/2012 | Bentley | |
| 8,323,278 B2 * | 12/2012 | Brecheen | A61B 17/42 606/45 |
| 8,500,771 B2 | 8/2013 | Isham | |
| 8,939,932 B2 | 1/2015 | McCloskey et al. | |
| 8,962,011 B2 | 2/2015 | Raspagliesi | |
| 2002/0019613 A1 | 2/2002 | Alexandersen | |
| 2003/0028097 A1 | 2/2003 | D'Amico et al. | |
| 2003/0120256 A1 | 6/2003 | Lary et al. | |
| 2008/0300619 A1 | 12/2008 | Isham | |
| 2011/0184314 A1 * | 7/2011 | Gonzalez | A61B 10/0291 600/569 |
| 2013/0211384 A1 | 8/2013 | Raspagliesi | |
| 2017/0014605 A1 * | 1/2017 | Schulz | A61M 29/00 |

FOREIGN PATENT DOCUMENTS

| | | |
|---|---|---|
| WO | 2003026681 A1 | 4/2003 |
| WO | 2019/094591 A1 | 5/2019 |

OTHER PUBLICATIONS

International Search Report, PCT/AU2018/051305, dated Feb. 11, 2019, 5 pages.
Written Opinion, PCT/AU2018/051305, dated Feb. 11, 2019, 5 pages.

* cited by examiner

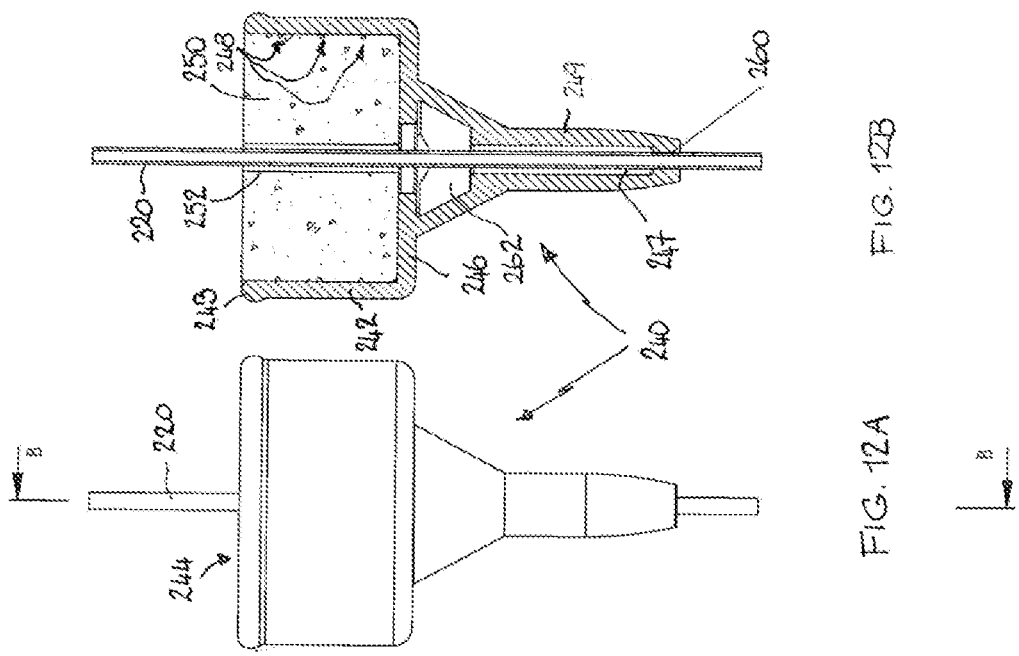
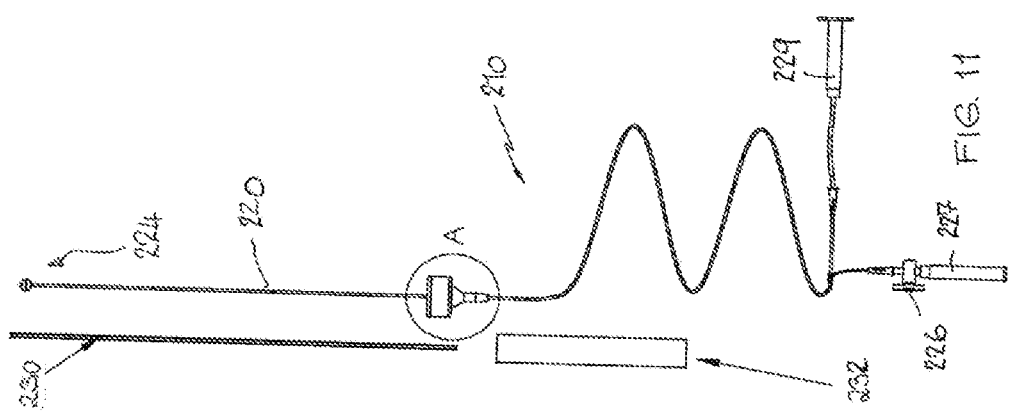

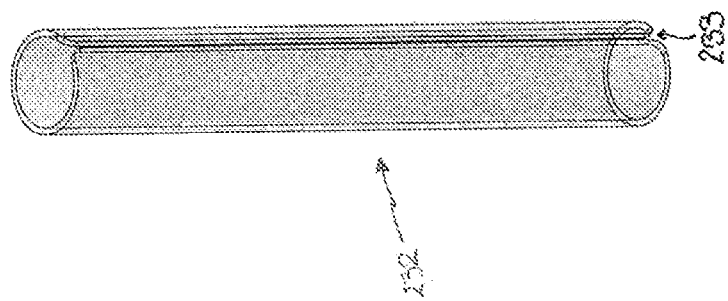
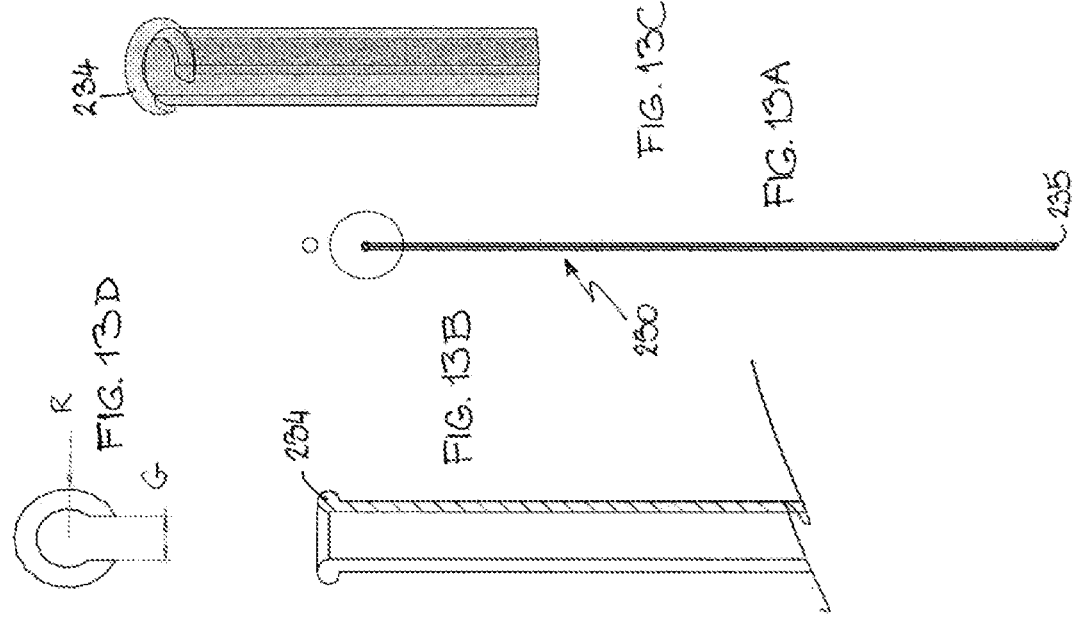

DEVICE FOR TREATMENT OF A BODY CANAL AND ADJACENT SURFACES

FIELD OF THE INVENTION

This invention relates to a device for treatment of a canal associated with an orifice of a human or animal body. The invention is of particular interest for the treatment of the endocervical canal and adjacent surfaces of a human cervix but in specific embodiments may be suitable for treating a human anal canal. A particular application of interest is the in situ inactivation of human papillomavirus (HPV) in the region of the uterine cervix or the anus.

BACKGROUND OF THE INVENTION

Human papillomaviruses occur worldwide, affecting humans and the animal kingdom. Of the genital types affecting humans there are high and low risk types. The high-risk types are linked to the development of low and high-grade dysplasia and cervical cancer. Oncogenic strains of HPV have been found in 99.7% of cervical cancers. They are also associated with vulval, anal and penile carcinoma. Low risk types are associated with genital wart and low-grade dysplasia. Worldwide it has been estimated that 325 million women have either subclinical HPV or HPV-related clinical lesions.

The uterine cervix is particularly vulnerable to the effects of HPV infection at the transformation zone, which is an area where the stratified squamous cells of the vagina change over to become the columnar cells lining the endocervix and uterus. Cervical dysplasia can be either squamous or glandular in origin. Squamous dysplasia is more common, but the frequency of glandular lesions is increasing. The area of cell changeover is termed the metaplastic area, and most HPV associated cervical lesions occur within this area.

The presence of persistent HPV infection is thought to be a prerequisite for the development and maintenance of second and third stage cervical intraepithelial neoplasia (CINIII), ie, severe or precancerous dysplasia.

A known treatment of severe uterine cervical dysplasia (squamous epithelial lesions or glandular) is surgical removal of the areas of the uterine cervix that may possibly be involved. Treatment initially requires cytology, colposcopy and biopsy, and then a surgical treatment such as laser excision, loop excision or cold coagulation of the uterine cervix.

Complications of surgical treatment of uterine cervical dysplasia include cervical stenosis, constriction and complete sealing of the os, pelvic endometriosis following hematometra, painful and prolonged menstruation, excessive eversion of columnar epithelium, infection, bleeding, pain, psychological morbidity, infertility, and an incompetent cervix. Disease may recur after treatment and even progress to invasive cancer. Some women are distressed by having Pap smear abnormalities even though they are not considered to be serious, and in order to alleviate their concerns, many women with low-grade lesions are unnecessarily treated. The other reason for unnecessary treatment of low grade lesions is the concern of the treating physician that the patient may fail to attend for further follow-up and consequently progress to high-grade disease.

The anus is also particularly vulnerable to the effects of human papillomavirus infection, particularly at the transformation zone where the stratified squamous cells of the anal verge change over to the columnar epithelial cells of the rectum.

Current treatment for anal dysplasia is either surgical removal or, in many cases, observational if severe extensive infection is present. If the dysplasia is very severe and involves the whole circumference of the anal canal, surgical treatment is to remove the whole area and provide a colostomy. Because the operation is so radical, and the duration of time to progress from anal dysplasia to anal cancer is not known, an observational approach is usually undertaken and the individual treated when cancer arises.

It is known that iodine in the form of povidone-iodine is effective in treating many viruses including bovine papillomavirus. The latter is reported in D. C. Sokal et al, "Inactivation of papillomavirus by low concentrations of povidone-iodine", *Sexually Transmitted Diseases* Vol 22, No. 1 (January-February 1995) 22-24, which suggests that povidone-iodine or other agents might reduce the rate of sexual transmission of the human papillomavirus associated with cervical cancer.

Povidone-iodine solution has relatively low tissue toxicity and has been used in topical formulations for disinfection, wound antisepsis, the treatment of burns, and the treatment of non-specific vaginitis. Povidone-iodine is available in over-the-counter preparations as a douche, vaginal gel, and vaginal suppository for the symptomatic treatment of minor vaginal irritation and itching.

By way of example, U.S. Pat. No. 5,035,883 discloses the use of povidone-iodine complex by applying an aqueous or aqueous alcoholic solution of the complex in the treatment of non-oral and non-periodontal human disorders. There is specific mention of vaginal infection and papillomavirus infection.

A form of iodine has been applied topically to the uterine cervix in the Schiller's test. In this test, Lugol's iodine is applied to the uterine cervix and the observed colour change is used to either detect HPV infected tissue or demarcate areas for treatment. The glycogen in fully differentiated genital epithelium takes up the iodine, staining the tissue dark brown. The application of iodine is used to distinguish between metaplasia (iodine negative) and HPV associated lesions (partial uptake).

A number of prior references describe intra-uterine catheters with single inflatable balloons, typically for sealing the entrance to the uterine cavity. For example, in Canadian patent 1,313,803, the balloon, which is inflated with the actual fluid being introduced into the uterine cavity, seals an extended region in the vicinity of the internal os. The devices of European patent publication 0088714 and U.S. Pat. No. 5,372,584 are generally similar save that the sealing balloon sits clearly within the uterine cavity immediately inwardly of the internal os.

Present applicant's prior international patent publication WO 2003/026681 (the contents of which are incorporated herein by reference) discloses a method of treating early papillomavirus infection of a uterine cervix or anal canal in which a viral inactivation agent, such as iodine, is applied under pressure to the endocervical canal or anal canal in an amount effective to inactivate a portion of the virus population infecting the canal. Also disclosed is a device for such treatment consisting of a hollow stem that carries an inflatable balloon for occluding the inner os and a cap for occluding the external os and adjacent external vaginal wall surfaces comprising the upper vaginal vault.

Present applicant's international patent publication WO 2010/099580 (the contents of which are incorporated herein by reference) discloses an immune stimulant composition particularly effective in treating a cervical or anal HPV infection. The immune stimulant composition comprises a combination of aluminium hydroxide and 3'-deacylated monophospholipid A (MPL).

It is an object of the invention to provide an improved or at least alternative device for treatment of a canal associated with an orifice of a human or animal body. In one or more embodiments of the invention, it is a particular object of the invention to provide an improved or at least alternative device for treatment of a human cervix, eg, with an HPV inactivation agent or immune stimulant composition.

Reference to any prior art in the specification is not an acknowledgment or suggestion that this prior art forms part of the common general knowledge in any jurisdiction.

SUMMARY OF THE INVENTION

In a first aspect, the invention provides a device for treatment of a canal associated with an orifice of a human or animal body, including:
- a stem portion adapted for insertion along the canal, which stem portion includes at least one fluid flow passage extending along the stem portion;
- an expandable member carried by the stem portion for occlusion of an inner end region of the canal;
- a cap slidably mounted on the stem portion, proximally of the expandable member and configured for occlusion of an outer end of the canal to thereby define, with the expandable member, a treatment cavity that includes the canal and surfaces about the outer end of the canal;
- one or more orifices in the stem portion through which treatment fluid is deliverable to the treatment cavity via said at least one fluid flow passage; and
- a fluid reservoir incorporated into the cap, which fluid reservoir is adapted to receive and store treatment fluid for contact with said surfaces about the outer end of the canal.

In accordance with a second aspect of the invention, there is provided, a device for treatment of a canal associated with an orifice of a human or animal body, including:
- a stem portion adapted for insertion along the canal, which stem portion includes at least one fluid flow passage extending therealong, the stem portion having a distal end;
- an expandable member carried by the stem portion at or adjacent the distal end for occlusion of an inner end region of the canal;
- a cap mounted on the stem portion, proximally of the expandable member and configured for occlusion of an outer end of the canal to thereby define, with the expandable member, a treatment cavity that includes the canal and surfaces about the outer end of the canal;
- one or more orifices through which treatment fluid is deliverable to the treatment cavity via said at least one fluid flow passage or via a second fluid flow passage; and
- a fluid reservoir incorporated into the cap, which fluid reservoir is adapted to receive and store treatment fluid for contact with said surfaces about the outer end of the canal.

Preferably, the reservoir comprises a receptacle portion of the cap. The receptacle portion may have its opening distally facing so as to cup the surfaces about the outer end of the canal i.e. the cervix in the most preferred application. The shape of the receptacle may be cylindrical, albeit traversed by the stem portion.

Preferably the cap includes drainage chamber disposed proximally of the receptacle portion.

The reservoir may comprise a fluid retention element. This may be in combination or as an alternative to the receptacle form of the reservoir. The fluid retention element preferably comprises an agent retaining material such as an open cell foam or polymer matrix. The fluid retention element may be a body of suitable fluid absorptive material, e.g., sponge material, in a medical grade material such as Medstock or Surgisponge. In an embodiment, this fluid absorptive body is held within the cap with an exposed annular surface thereof about the stem portion. In a most preferred form of the invention, the fluid retention element is received in the receptacle portion. The fluid retention element could also be in cartridge or capsule form.

The stem portion is preferably a flexible body for minimal discomfort of the patient. The stem portion is preferably relatively thin compared to the canal. This minimise coverage of the treatment surfaces and allows the treatment to be more effective. The stem portion is preferably a catheter closed at the distal end. The preferred catheter size is within the range of 5, 6, and 7 French. Suitably, the catheter is long enough to extend beyond the body, e.g. 60 cm. The catheter may be a single or double lumen catheter.

The device may further include an introducer for introducing the stem into the body e.g. a tube formed in a medical grade polymer, that receives the stem portion for free movement along its bore. The stem portion may be slidable within and relative to the introducer. The introducer is suitably relatively more rigid than the stem portion to aid insertion.

In one form of the invention, the cap may be slidable relative to the introducer so that the cap extends around the introducer.

However, it is preferable that the introducer is removable. The introducer is removable by means of a slitted, perforable or frangible construction. Preferably, the introducer has a lengthwise slit. The introducer preferably extends beyond the body.

It is preferred that the stem portion and the cap have a sliding, sealing fit therebetween.

An insertion tool is provided for pushing the cap distally. The insertion tool is removable by means of a slitted, perforable or frangible construction.

The expandable member is preferably an inflatable balloon and the stem portion with the balloon may conveniently be a balloon angiocatheter.

The body canal may be an endocervical canal or an anal canal.

In accordance with a third aspect of the present invention, there is provided, a device for treatment of a canal associated with an orifice of a human or animal body, including:
- a flexible stem portion adapted for insertion along the canal, the stem portion having a distal end;
- an expandable member carried by the stem portion at or adjacent the distal end, the expandable member for occlusion of an inner end region of the canal; and
- a cap portion mounted on the stem portion, proximally of the expandable member and configured as a receptacle, open distally, to close an outer end of the canal and to accommodate the surface(s) about the outer end of the canal to thereby define with the expandable member, a treatment zone between the expandable member and the cap portion, wherein the receptacle is adapted to receive and store treatment fluid for contact with the surface(s) about the outer end of the canal.

Any of the features described above in connection with the first and second aspects of the invention, may have application to the third aspect of the invention.

In accordance with a fourth aspect of the present invention, there is provided, a device for treatment of a canal associated with an orifice of a human or animal body, including:

a thin flexible stem portion adapted for insertion along the canal, the stem portion having a distal end;

an expandable member carried by the stem portion at or adjacent the distal end, the expandable member for occlusion of an inner end region of the canal;

a cap portion mounted on the stem portion, proximally of the expandable member to close an outer end of the canal and to accommodate the surface(s) about the outer end of the canal to thereby define with the expandable member, a treatment zone between the expandable member and the cap portion, wherein the cap portion includes a fluid retention element to receive and store treatment fluid for contact with the surface(s) about the outer end of the canal.

Any of the features described above in connection with the first and second aspects of the invention, may have application to the fourth aspect of the invention.

With particular reference to the third and fourth aspects of the invention (but not limited thereto), the cap portion and stem portion may have a fixed spacing therebetween. For example, the set spacing may be any of 2, 3, 3.5 cm, or 4 cm. The selection of the suitable device by the treating physician may depend upon the size and age of the patient. This is particularly suited for insertion by minimally or non-medically trained staff such as in a field hospital. The cap portion and stem portion may be integrally formed. The treatment fluid may be pre-loaded into the receptacle (third aspect) or the fluid retention element (fourth aspect).

With particular reference to the second, third and fourth aspects above (but not limited thereto) which recite that the expandable member is carried by the stem portion at or adjacent the distal end, reference to "adjacent" is intended to mean very close to the distal end as is practicable. For instance, the catheter form of the stem portion may be closed by a cap and the expandable member is adjacent the cap. The intention of the expandable member being at or adjacent the distal end of the stem portion is to avoid any unnecessary entry into the uterine cavity. This may cause negative consequences not limited to but including: risk of trauma including perforation of the uterus; added risk during pregnancy; unnecessarily invasive; increased risk of infection and bleeding which could interfere with the treatment program.

Other aspects of the invention may relate to a treatment method for inserting the device of the third and fourth aspects into the patient. In one preferred form of the invention, such a treatment method may involve repositioning the human or animal during treatment.

In accordance with a fifth aspect of the present invention, there is provided, a method of treating a canal associated with an orifice of a human or animal body, including:

inserting a stem portion along the canal;

expanding an expandable member carried by the stem portion to occlude an inner end region of the canal;

distally sliding a cap which is mounted on the stem portion proximally of the expandable member to occlude an outer end of the canal to thereby define, with the expandable member, a treatment cavity that includes the canal and surface(s) about the outer end of the canal, wherein a fluid reservoir is incorporated into the cap, which fluid reservoir is adapted to receive and store treatment fluid;

delivering treatment fluid to the treatment cavity such that treatment fluid received and stored in the reservoir contacts said surface(s) about the outer end of the canal.

Preferably the stem portion includes at least one fluid flow passage extending therealong and treatment fluid is delivered to the treatment cavity via said at least one fluid flow passage. The method may further include using an introducer for introducing the stem portion into the body, the stem portion being slidable relative to the introducer. The method may further include removing the introducer from the stem portion.

In a preferred form of the invention, the method includes using an insertion tool for distally sliding the cap.

In one preferred form of the invention, the treatment method may involve repositioning the human or animal during treatment.

Any of the features described above in connection with the first and second aspects of the invention, may have application to the fourth aspect of the invention.

As used herein, except where the context requires otherwise, the term "comprise" and variations of the term, such as "comprising", "comprises" and "comprised", are not intended to exclude further additives, components, integers or steps.

It will be understood that the invention disclosed and defined in this specification extends to all alternative combinations of two or more of the individual features mentioned or evident from the text or drawings. All of these different combinations constitute various alternative aspects of the invention.

Further aspects of the present invention and further embodiments of the aspects described in the preceding paragraphs will become apparent from the following description, given by way of example and with reference to the accompanying drawings.

BRIEF DESCRIPTION OF THE DRAWINGS

The invention will now be further described, by way of example only, with reference to the accompanying drawings, in which:

FIG. 11 is a diagram of the device in accordance with a second embodiment of the invention;

FIG. 12A is a detailed view of A of FIG. 11;

FIG. 12B is a cross-sectional view through B-B of FIG. 12A;

FIG. 13A is an illustration of the introducer according to the second preferred embodiment of FIG. 11;

FIG. 13B is a cross-section through O at the top end of the introducer;

FIG. 13C is a perspective view of O of FIG. 13A;

FIG. 13D is a top view of the introducer of FIG. 13A;

FIG. 14 is a perspective view of the insertion tool of the second preferred embodiment of the device of FIG. 11;

DESCRIPTION OF EMBODIMENTS OF THE INVENTION

Figure 1:
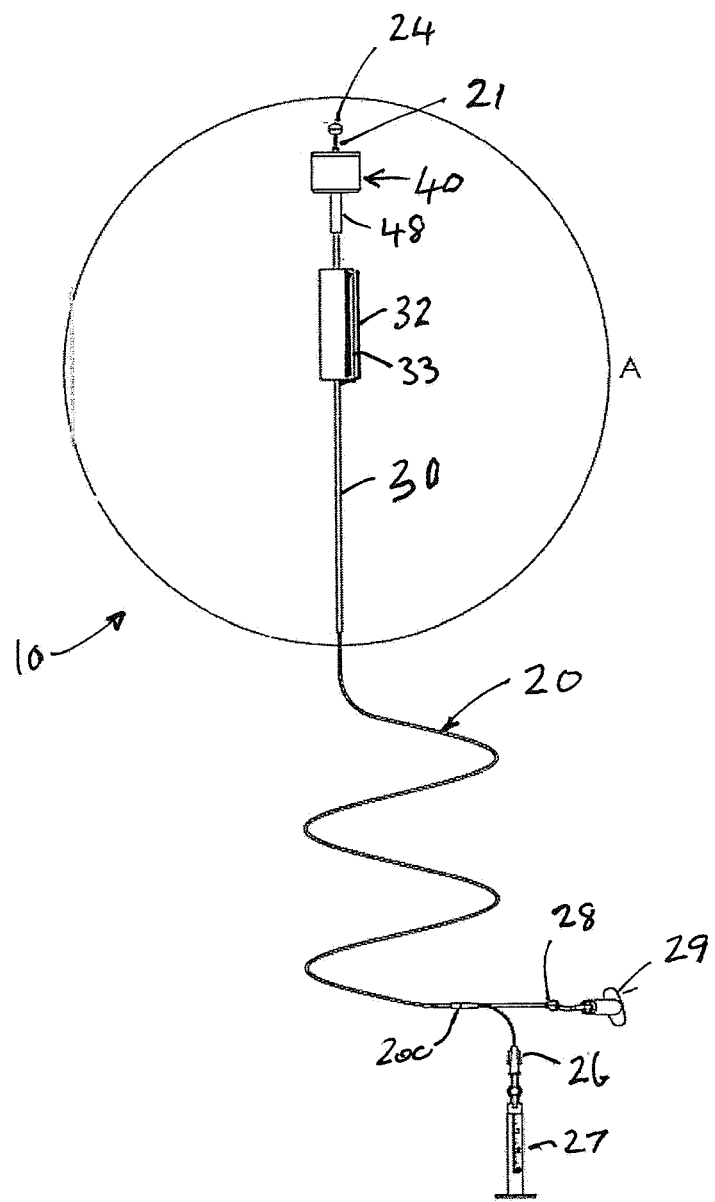
FIG. 1 is a diagram of a device in accordance with a first embodiment of the invention for treating a human cervix with a virucidal composition, e.g. in order to reduce or eliminate HPV infection, or for stimulating the immune system.
Figure 2:
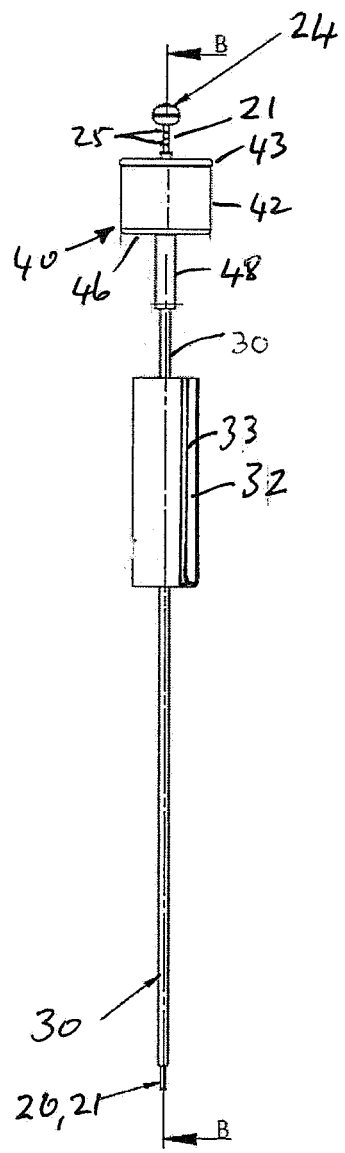
FIG. 2 is an enlargement of region A of FIG. 1.
Figure 3:
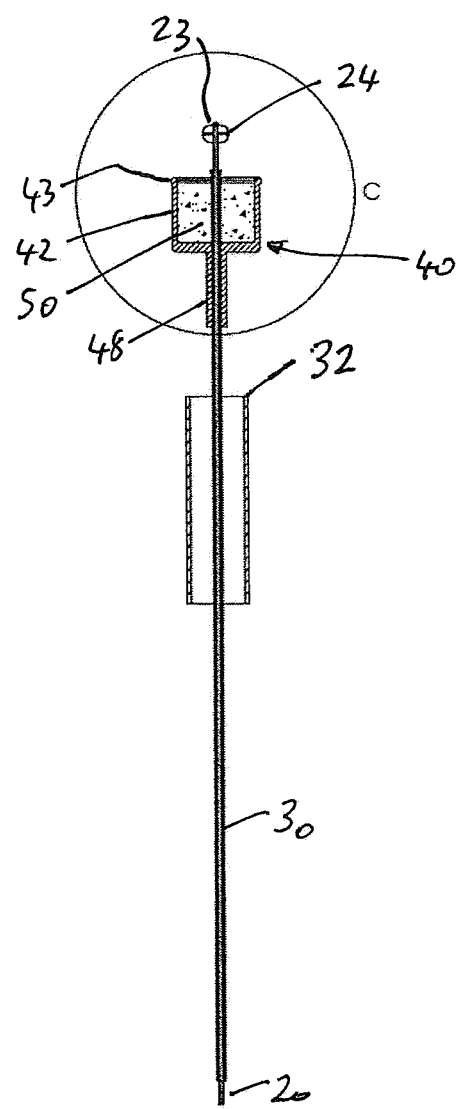
FIG. 3 is a cross-section on the line B-B in FIG. 2.

Embodiment of First Embodiment of FIGS. 1 to 6

The illustrated device 10 is designed specifically for the treatment of a human uterine cervix with a virucidal composition in the form of a HPV inactivation agent e.g. povidone-iodine or Lugol's-iodine, or an immune stimulant. The device includes a balloon angiocatheter 20 which has been used for testing proof of concept. However, the catheter need not be provided in the form of an angiocatheter and other types of medical grade catheters may be employed in the present invention. The catheter 20 provides a stem portion 21 adapted for insertion along a cervical canal and, at a distal location on the catheter 20 adjacent its distal end 22, an occlusion device such as inflatable balloon 24. For this purpose, the catheter may be provided with a first lumen. For the introduction of treatment fluid, a second lumen may be provided in the catheter. A third lumen may be used for an additional treatment fluid.

Figure 5:
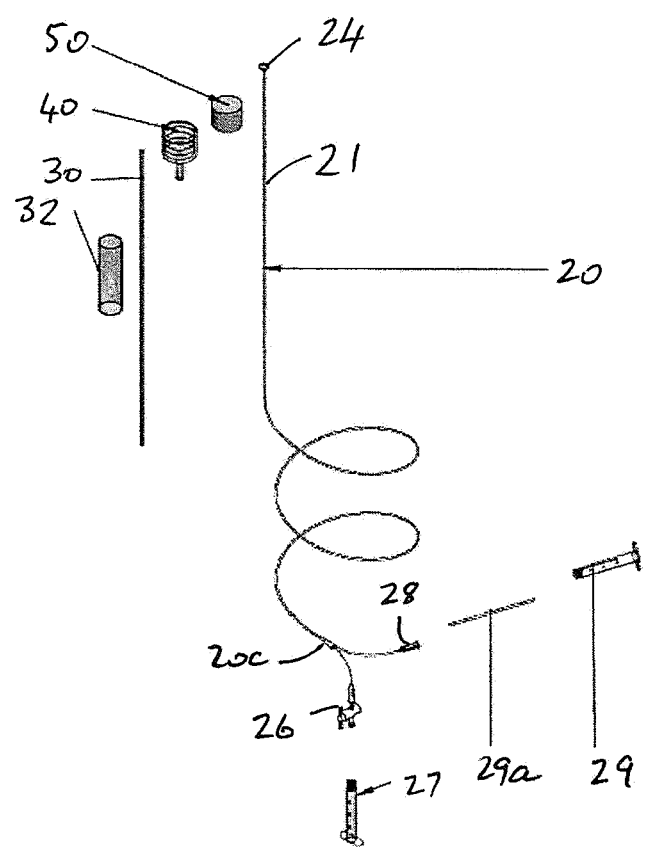
FIG. 5 is a fragmentary view showing the separated principal components of the device of FIGS. 1 to 4.

The device further includes a tubular introducer 30 and an associated insertion tool 32, and a cervical cap 40. The separated components are shown in FIG. 5 and their assembly depicted in FIG. 1.

Figure 4:
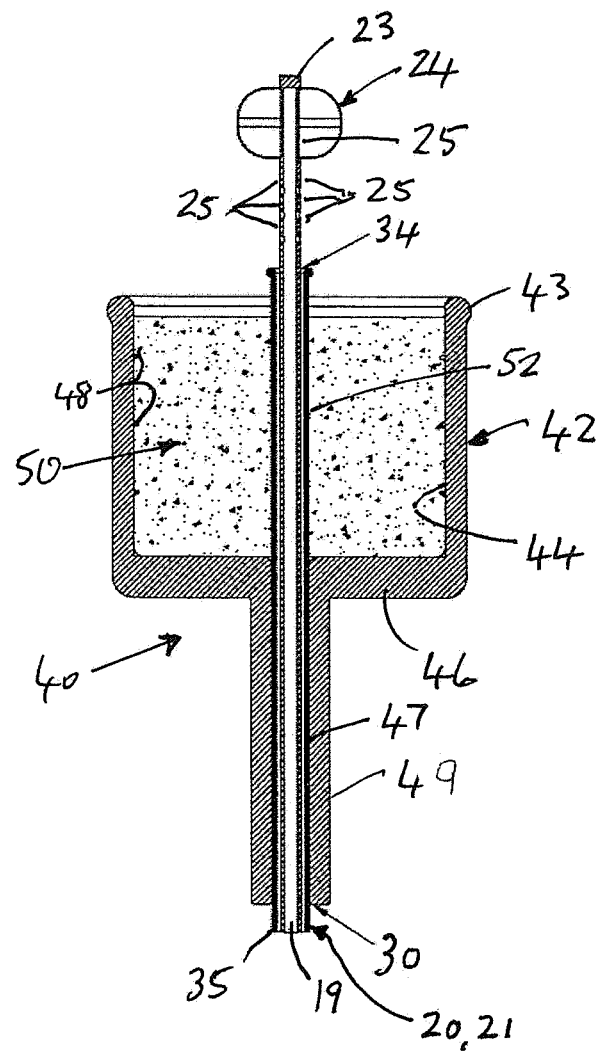
FIG. 4 is an enlargement of region C of FIG. 3.

The introducer 30, is a Teflon™ coated medical grade high density polyethylene (HDPE) tube with beaded or rounded end rims 34, 35 (FIG. 4). This tube receives the catheter 20 with sufficient tolerance to allow the catheter 20 to freely slide along the introducer without damage to the uninflated balloon 24, which is a fine membrane of material flat on a reduced diameter end portion of the catheter 20. In all of the figures, balloon 24 is shown in its inflated condition for ease of understanding but it would only be inflated for testing or in situ. The distal end of the catheter abutting the balloon has a solid end closure 23.

Figure 6:
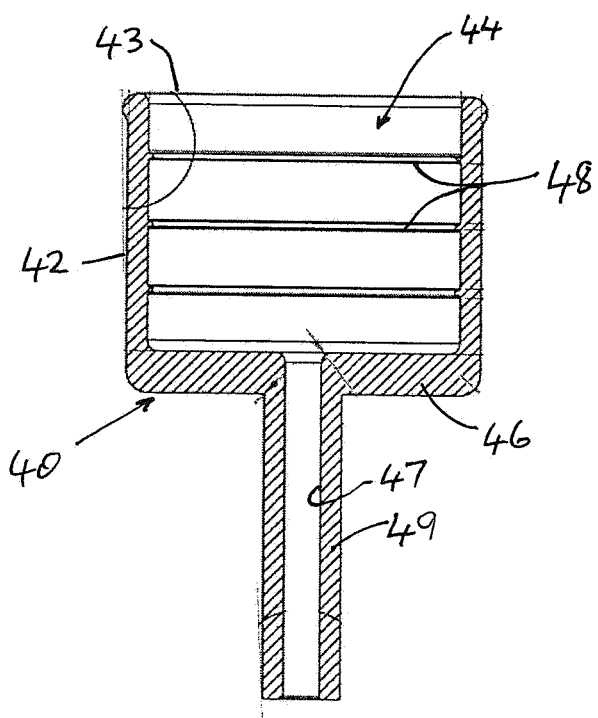
FIG. 6 is a more detailed cross-section of the cervical cap component of the device.

Cervical cap 40, in this embodiment, is a cylindrical body 42 about a receptacle or chamber 44 (FIGS. 4 and 6). Cervical cap 40 is a flexible body made of a resiliently flexible plastics material, more preferably a biocompatible medical grade plastic such as medical grade silicone. The cervical cap 40 is preferably able to flex and conform to the shape of the cervix. The inside of the receptacle 44 is sized to receive the cervix and different size caps are available to be selected by the treating physical according to the physical attributes of the patient. Size ranges include 26-30 mm inside diameter of the receptacle 44.

The cervical cap 40 is wholly open at one end defined by a beaded rim 43 of cylindrical body 42, and partially closed at the other by an annular wall 46. A tubular stem portion 49 of cap 40 depends from annular wall 46 and they together define a longitudinal coaxial bore 47 that is of slightly smaller diameter than the external diameter of the introducer 30 so as to receive the introducer in a tight fit that seals against leakage of fluid from receptacle/chamber 44. The assembly of the two is such that the distal beaded rim 34 of the introducer is disposed slightly proud of or level with the beaded rim 43 of the cap. Beaded rim 34 provides a rounded surface in order to avoid damaging the external cervical os and also prevents the introducer 30 being pulled back through the cap.

Insertion tool 32 comprises a sleeve with a full length longitudinally slit 33. The sleeve is thereby resiliently laterally expandable and can be fitted about the introducer 30 for engaging the underside of annular wall 46 of the cap 40, for pushing the cap 40 into engagement with the vaginal vault and cervix. The slitted form also allows the insertion tool 32 to be withdrawn once the cap 40 is in place.

Catheter 20 has, towards its distal end adjacent the balloon 24, respective diametrically opposite sets of three longitudinally spaced radial orifices 25a through which treatment liquid may be delivered out of the catheter 20 via its longitudinal central bore 19. Further fine orifices (not visible) from bore 19 are provided within the membrane of balloon 24, which itself is sealingly adhered to the surface of the catheter at spaced annular interfaces. At its proximal end, catheter 20 has respective valve-controlled ports 26, 28 in fluid communication with the bore 19. For this application, port 26 receives a syringe 27 for introducing air to inflate balloon 24, while port 28 receives a suitable syringe 29 for introducing a treatment liquid such as povidone-iodine into the catheter bore 19. Balloon angiocatheter 20 may be a commercially available product such as the Berman Angiographic Balloon Catheter, for example size 5 Fr, 6 Fr or 7 Fr.

As explained in the aforementioned international patent publication WO 2003/026681, it is preferable for the HPV inactivation agent such as Lugol's iodine or povidone-iodine to be infused under sufficient pressure to expand the endocervical canal to ensure that all surfaces, including glandular surfaces, are in close proximity to the solution including the ectocervix, the glandular endocervix and adjacent parts of the upper vaginal vault. The agent may be delivered under pressure by a pressure pump/infuser such as the Go Medical Springfusor® Syringe Infusion Pump 29 and Flow Control Tubing (FCT) 29a. The infusion pump 29 has an operating pressure of approximately 1132 mmHg. A suitable range of operating pressures is between about 1100 mmHg and 1160 mmHg. It is further thought that pressure cycling may be desirable to ensure that the solution in the canal remains at maximum concentration. The concentration and pressure of the solution is selected to ensure an effective virucidal concentration is achieved from the external epithelium to the basal cell layer.

As foreshadowed earlier, the device may also be used to apply immune stimulant or other virucidal solutions to treat HPV and pre-cancer.

In accordance with the invention, it has been found desirable, for optimising control of the treatment, to incorporate a reservoir in the cap adapted to receive and store treatment fluid and to contact surfaces about the outer end of the endocervical canal, ie the external os, for applying the stored treatment fluid to those surfaces. In the present embodiment, the reservoir is in the form of a receptacle or chamber 44 and a fluid retention element in the form of an absorptive body or sponge 50 of a suitable medical grade material such as Medstock or Surgisponge. The sponge occupies chamber 44 below beaded rim 43 and has an axially centred bore 52 to receive the introducer 30. The sponge 50 is a separate body forced into chamber 44 and retained in place by three equally spaced shallow annular ribs 48 (FIG. 6) formed integrally on the inner wall of the cylindrical body 42 of cap 40. Sponge 50 may sit flush with, be recessed behind, or be raised above, the top of cap rim 43, whichever is determined to give optimum outcomes.

In another form of the invention (not shown), the sponge may be flat in form where it is intended to overlay parts of the vaginal wall, depending on the treatment desired. In this version, the flat sponge may be pushed into the vagina by the cap as it is inserted.

Sponge Forms

Figure 7A:
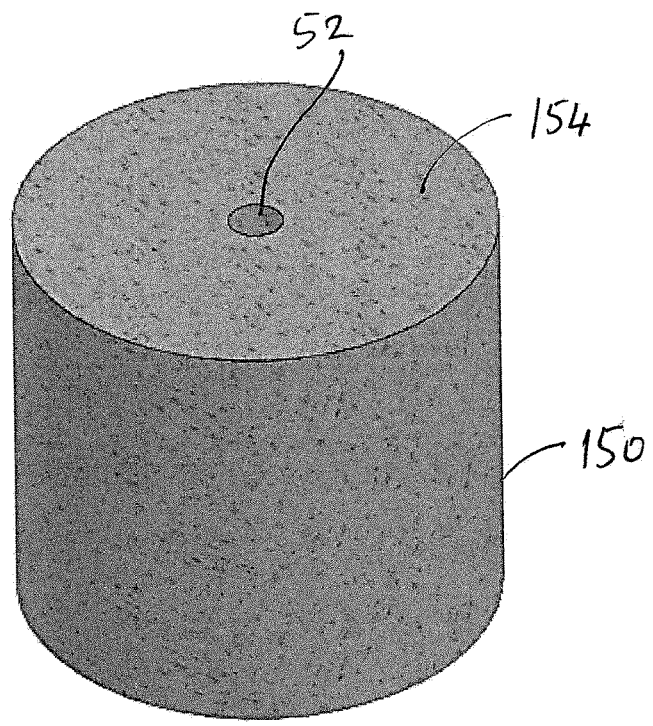
FIGS. 7A and 7B depict an alternative form of sponge.
Figure 7B:
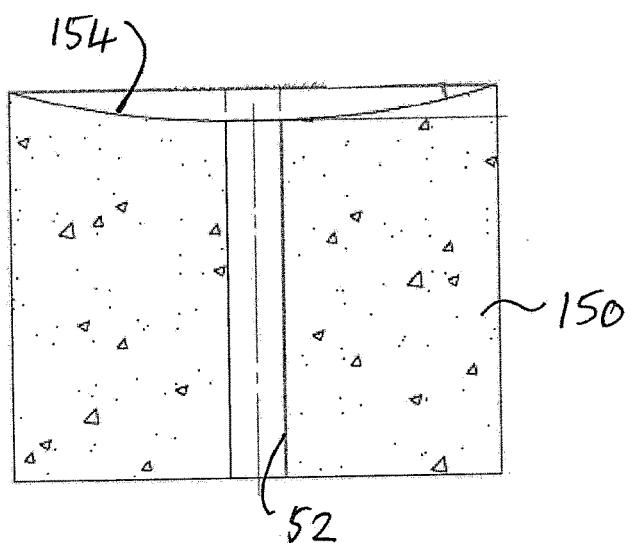

FIGS. 7A and 7B depict an alternative and preferred form of sponge 150 shaped with a depression or concavity 154 to better embrace and seat the vaginal vault surfaces and the protruding cervix at the external os.

Figure 8:
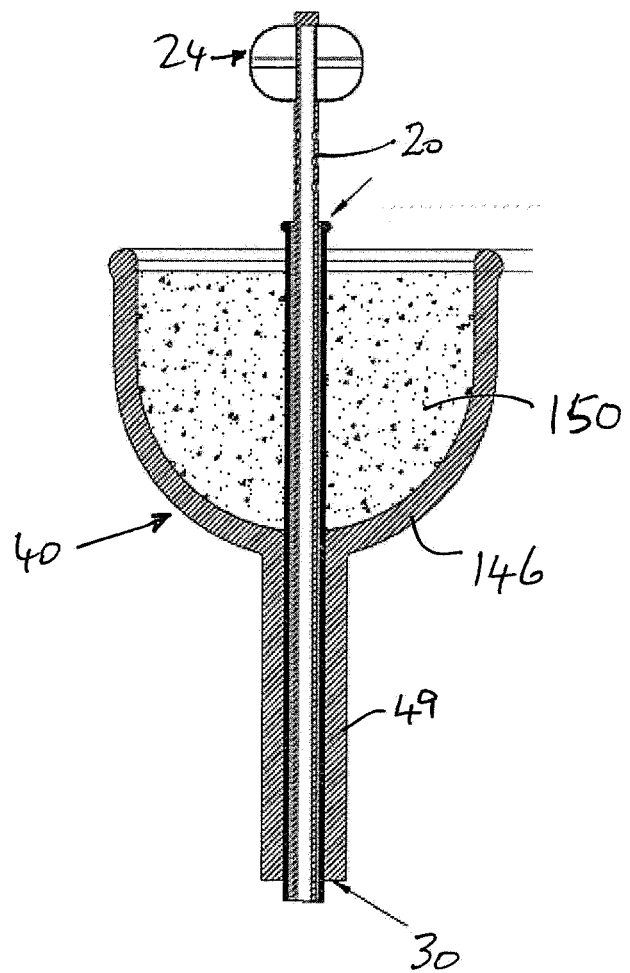
FIG. 8 is a view corresponding to FIG. 4 that shows an alternative embodiment of the cervical cap and its contained sponge.

Embodiment of FIG. 8

FIG. 8 shows an alternative embodiments of the cervical cap and its contained sponge, in which the end wall 146 is domed rather than flat, and the sponge 150 correspondingly shaped.

Treatment Procedure According to First Embodiment

Figure 9:
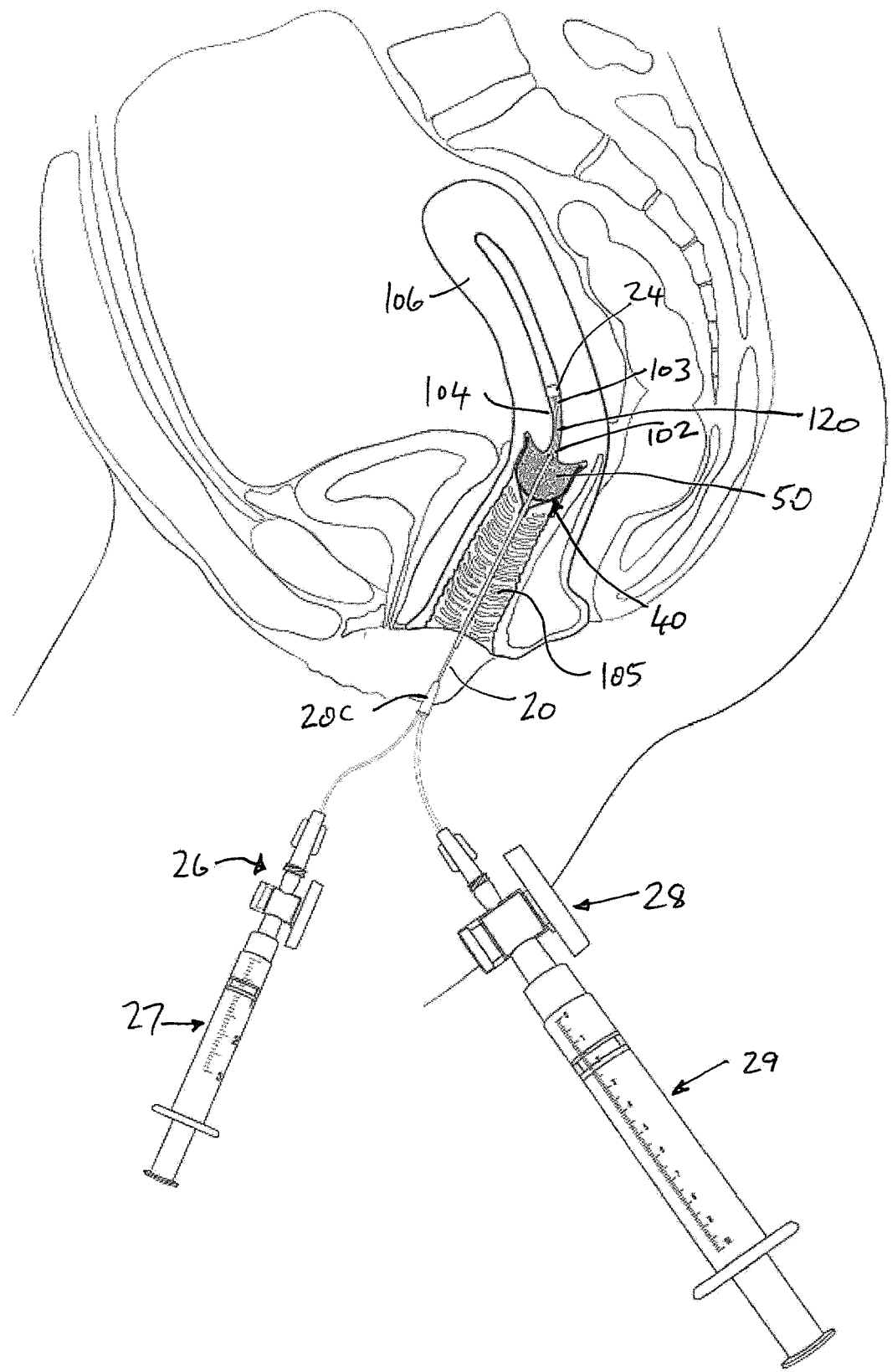
FIG. 9 illustrates the device of FIGS. 1 to 4 but with a cervical cap as in FIG. 8 and a sponge with a top surface concavity, in situ in a human uterine cervix during treatment of the cervix with HPV inactivation agent.
Figure 10:
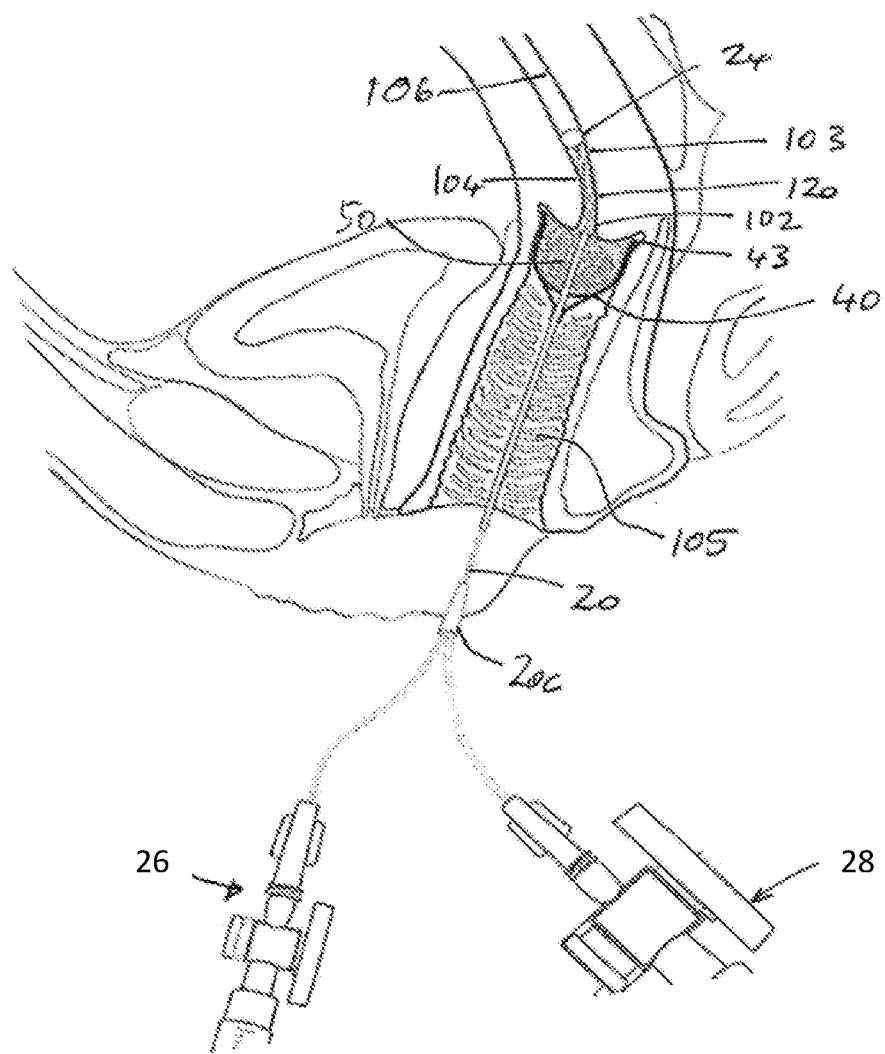
FIG. 10 is an enlargement of part of FIG. 9.

The preferred treatment procedure utilising the illustrated device of FIGS. 1 to 8 will now be set out in detail, with reference to the anatomical cross-section of FIG. 9, partially enlarged in FIG. 10.

The treating physician will start with a sterile pack, or set of packs, of the separate components of the device, ie the balloon catheter 20, introducer 30, insertion tool 32 and cervical cap 40, along with syringes 27 and 29 (or infusion pump). The cap will typically include the sponge 50 already in place.

The treating physician commences by pushing the introducer 30 through the cap 40 and then pushing the catheter 20, with balloon 24 deflated, through the introducer 30 until the balloon 24 protrudes from the distal end of the introducer 30. It is important to use syringe 27 to inflate and then deflate balloon 24 to ensure its integrity, i.e. to verify that it has not been damaged in the assembly process. Once the balloon 24 is deflated, the catheter 20 is retracted so that the balloon 24 is withdrawn into the introducer 30, ready for insertion into the vagina. The balloon 24 and the introducer 30 may have alignment features to indicate the correct relative alignment for introduction. The alignment features may be in the form of indicia or indicium such as registration marks (not shown) on the catheter and the introducer 30. For instance, the introducer 30 may be of clear plastic and marked with the required relative location of the catheter for insertion i.e. the relative insertion configuration. Alternatively, the registration mark on the catheter 20 may align with the proximal end of the introducer tube to mark the insertion configuration.

The sponge 50 is pre-wetted with the iodine treatment solution, e.g. povidone-iodine, typically by gently pouring the liquid onto the sponge in the cap. The physician also pre-primes the catheter with treatment solution using syringe 29 before insertion into the body (typically about 0.5 ml of fluid).

The physician then introduces a vaginal speculum (not shown) into the vagina 105 of the patient, and via the speculum pushes the introducer 30 with the catheter 20 into the vagina until the introducer reaches the external cervical os 102 or short thereof. The introducer 30 is required because the catheter 20 is generally too flexible to be inserted through the vagina and the introducer 30 serves as a guide for the catheter through the vagina. The beaded distal end 34 of the introducer prevents the distal end of the introducer 30 extending further into the endocervical canal 104 and also prevents abrasion of the cervix. Any bleeding or trauma of the patient will compromise treatment and give rise to possible infection.

Once the introducer 30 is positioned at the external cervical os 102 or short thereof, the catheter 20 is moved relative to the introducer 30 through the external os 102 and endocervical canal 104 until he or she is confident by "feel" that the balloon is clearly in the uterus 106. The extension of the balloon 24 beyond the distal end of the introducer 30 may be up to 3 cm. A further registration mark on the catheter may be provided to align with the registration mark on the introducer or the proximal end of the introducer to indicate the required extension of the catheter to seat the balloon 24 in the intended position. The balloon 24 is then inflated by introduction of air via syringe 27 and the catheter 20 pulled back (tugged gently) to firmly engage the inflated balloon in the uterus against the internal os 103. This is the "seated" position of the balloon 24.

In the second embodiment shown in FIGS. 11-16, the introducer 230 is removed at this stage or after inflation of the balloon 224 and before withdrawal of the catheter 220 to the seated position. See discussion below concerning FIGS. 11-16.

Syringe 29 is now employed to introduce treatment solution into the treatment cavity, such as Lugol's iodine, povidone-iodine or an immune stimulant composition, via the bore of the catheter 20 and the orifices 25. A suitable syringe 29 is a Go Medical Springfusor® Syringe Infusion Pump and Flow Control Tubing (FCT) 29a for introducing the treatment liquid at a rate of 10 ml/30 min. The solution is introduced with tension maintained on the catheter 20 and thereby the inflated balloon 24, until solution is seen emerging from the external os. The tension may be applied by manual pulling of the catheter 20.

Once the solution is seen at the external os, the insertion tool 32, is employed to push the cap 40 along the introducer 30 into firm engagement with the vaginal vault 110 about the protruding cervix 112. Once the cap is so fitted, the insertion tool is then withdrawn and removed, an action facilitated by slit 33 as earlier described, and the introducer is retracted to the bottom of the cap 40 so that it does not damage the cervical os or restrict the area of treatment. The bead 34 prevents it from being withdrawn completely from the cap 40.

A treatment cavity 120 is thereby defined between the cap and the balloon, and includes the entire endocervical canal 104 and the surfaces 114 of the cervix and vaginal vault about the external os 102. Treatment solution stored in the sponge is already being applied to surfaces 114, and although not essential, concave shaping of the exposed surface of sponge 50 as in FIGS. 7A and 7B ensures that the sponge and thereby the treatment solution retained therein is optimally in contact with those surfaces 114.

The speculum is now removed and the treatment solution is maintained under substantially constant pressure. FIGS. 9 and 10 depict the arrangement at this stage of the procedure. To maintain the treatment cavity under pressure, seals need to be provided between the catheter 20 and the introducer 30 as well as between the introducer 30 and the cap 40. This is simplified in the embodiment of FIGS. 11 to 16 below whereby a seal is only required between the catheter 320 and the cap 340 because the introducer 330 is removed before the cap 340 is seated against the cervix.

The Springfusor™ 29 has an operating pressure of approximately 1132 mmHg. To some extent, the pressure may expand the canal to ensure that all surfaces, including glandular surfaces, are in close proximity to the solution including the ectocervix, the glandular endocervix and adjacent parts of the upper vaginal vault. However, the expansion of the cervical canal to any great extent may be undesirable because this may cause discomfort in patients. In addition to pressure or as an alternative thereto, the patient's position may be shifted to ensure adequate and preferably even distribution of the treatment fluid onto the surfaces of the cervical canal. For example, the patient may lie of one side for half the treatment time and on the other side for the remainder of the treatment time. The treatment surface or bed may also be arranged on an incline at the start of the treatment.

It is thought that pressure cycling may assist to ensure that the solution in the canal remains at maximum concentration. In the case of a virucidal solution such as Lugol's iodine or povidone iodine, the concentration and pressure of the solution are selected to ensure an effective virucidal concentration is achieved from the external epithelium to the basal cell layer. At present, patient movement is preferred over pressure cycling.

At the end of treatment the vaginal speculum is reintroduced for visualising the device, the balloon is deflated by drawing the air back into the syringe, and then the whole device is removed via the speculum, which is itself then withdrawn.

The optimum duration of treatment, typically timed from the placement of cap 40, will be determined by clinical trial and experience, but may be in the range 10 to 60 minutes. For example, it is presently thought that 10 to 20 minutes will be suitable with Lupol's iodine, while povidone iodine would likely require a longer period, e.g. up to 1 hour. The duration will typically depend on a range of factors including the concentration of the solution and its exact nature. The amount of fluid introduced over the treatment duration is about 2 ml.

Description of Second Embodiment of FIGS. 11 to 16

FIGS. 11 to 16 illustrate a second preferred embodiment of the device 210 according to a second preferred embodiment of the present invention. Because the device 210 is similar in many respects to the device 10 of the first embodiment, like numerals are used to represent like parts, except preceded by a '2' to indicate the second embodiment.

In the second embodiment of the device 210, the introducer 230 is intended to be removable while the balloon catheter 220 is in situ. The removable form of the introducer 230 will be described in connection with FIG. 13. The introducer 230 is removed before the cervical cap 240 is positioned against the cervix. Thus, the cap 240 is intended to form a tight seal around the catheter 220 to prevent leakage of the treatment fluid during treatment. For this reason, the proximal end 260 of the tubular stem portion 249 forms a tight fit around the catheter 220. For example, the opening at the proximal end 260 may have an inside diameter of 1.8 mm. However, the outside diameter of the catheter 220 may be alternatively 5, 6 or 7 French. At the time of writing, testing is still required to determine whether this tight fit will damage the balloon or conversely whether the balloon would damage the tight fit.

The tight fit between the catheter 220 and the lower constriction in the cap 240 may place the portion of the catheter between the balloon 224 and the cap 240 in tension. This tension should hold the balloon 224 and cap 240 in place and prevent leakage of fluid into the uterus. It is highly desirable to contain the treatment fluid within the treatment cavity, to stop spillage of toxic chemicals into the uterus and avoid chemical burns into the vagina.

FIG. 12B also illustrates a drainage chamber 262 beneath the receptacle 244 which contains the sponge 250. The drainage chamber is to help prevent leakage by providing a buffer for treatment fluid before being forced down the bore 247. The drainage chamber 262 is frusto-conical in shape with the widest portion arranged distally. The annular wall 246 overhangs the top of the chainage chamber 262. Structure extending from the annular wall 246 may also extend to the catheter 220 to act as a guide to the catheter 220. This prevents the catheter 220 from buckling the annular wall 246 and deforming the silicone cap 240, which by the nature of the material is resiliently flexible and tending to floppy.

FIG. 13 illustrates the slitted form of the introducer 230. The introducer is an elongate member with a C-shaped cross-section as shown in FIG. 13D. The cross-section is uniform throughout the length, apart from a beaded distal end 234 and a beaded proximal end 235. The introducer 230 has an internal diameter which allows a sliding fit along the catheter 220. The spacing of the gap G is sufficient to enable the introducer 230 to be stripped away from the catheter 220 without too much resistance which would cause discomfort to the patient in which the balloon catheter 220 has been inserted. On the other hand, the gap G is not so wide that the introducer 230 would easily slip off the catheter 220. The recommended gap G is therefore about 2 mm. The outside diameter of the bead is approximately 4.4 mm, where the outside diameter of the introducer is 3.6 mm (without the bead).

FIG. 14 illustrates the form of the insertion tool 232 having the longitudinal slit 233. The insertion tool is shaped to accommodate the tubular stem portion 249 of the cap 240 and bear against the proximal side of the annular wall 246 to push the cap 240 into position.

Figure 15:
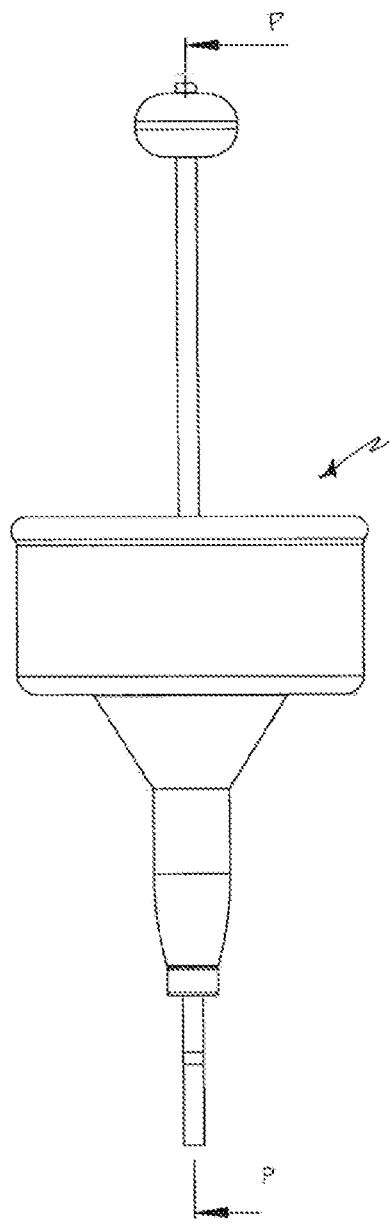
FIG. 15 is a variant of the device of FIG. 11.
Figure 16:
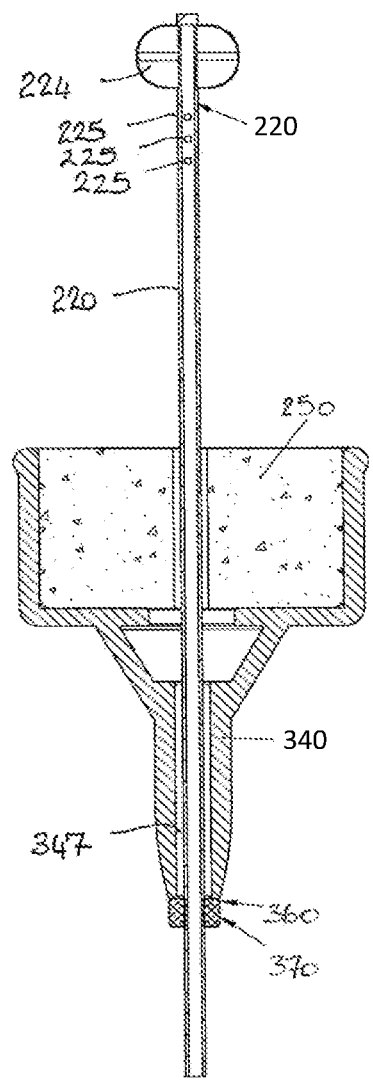
FIG. 16 is a cross-sectional view through P-P of FIG. 15.

FIGS. 15 and 16 show an alternative form of the cap 340 intended for use of the device 210. The cap 340 is similar in most respects to the cap 240, except at the proximal end of the cap where the stem portion 349 engages with the catheter 220. In this adaptation, an O-ring 370 is provided to seal around the catheter 220 and to seal the proximal end of the bore 347 to prevent leakage into the vagina. At the time of writing, the O-ring 370 had not been tested to determine whether or not it would damage the balloon 224.

The foregoing describes only some embodiments of the present invention and it will be evident to the person skilled in the art that modifications may be made thereto without departing from the scope of the present invention. For example, there are various ways of creating a seal between the catheter and the cap and the foregoing embodiments only disclose only a few ways of achieving this.

The invention claimed is:

1. A device for treatment of a canal associated with an orifice of a human or animal body, including:
    a stem portion adapted for insertion along the canal, which stem portion includes at least one fluid flow passage extending along the stem portion;
    an expandable member carried by the stem portion for occlusion of an inner end region of the canal;
    a cap slidably mountable on the stem portion, proximally of the expandable member and configured as a receptacle portion, open distally, for occlusion of an outer end of the canal to thereby define, with the expandable member, a treatment cavity that includes the canal and surface(s) about the outer end of the canal;

one or more orifices in the stem portion through which treatment fluid is deliverable to the treatment cavity via said at least one fluid flow passage;

a fluid reservoir incorporated into the cap, which fluid reservoir is adapted to receive and store treatment fluid for contact with said surfaces about the outer end of the canal; and an introducer for introducing the stem portion and expandable member into the body, the stem portion being slidable within and relative to the introducer, and wherein the cap is slidable relative to the introducer with a sealing fit therebetween.

2. The device as claimed in claim 1 wherein the stem portion has a distal end and the expandable member is carried by the stem portion at or adjacent the distal end.

3. The device as claimed in claim 1 wherein the reservoir is defined by the receptacle portion of the cap.

4. The device as claimed in claim 3 wherein the cap includes a drainage chamber disposed proximally of the receptacle portion.

5. The device as claimed in claim 3 wherein the reservoir comprises or includes a fluid retention element.

6. The device as claimed in claim 5 wherein the fluid retention element comprises an agent retaining material.

7. The device as claimed in claim 5, wherein the fluid retention element is received in the receptacle portion.

8. The device as claimed in claim 1 wherein the stem portion is a catheter closed at the distal end.

9. The device as claimed in claim 8 wherein the stem portion and the expandable member define a balloon catheter.

10. The device as claimed in claim 1 wherein the introducer is relatively more rigid than the stem portion.

11. The treatment device as claimed in claim 1 wherein the cap comprises a resiliently flexible body and the receptacle portion is sized to receive the cervix with the receptacle portion having an inside diameter in the range of 26-30 mm.

12. The treatment device as claimed in claim 11 wherein the distal end of the cap has an open end defined by a beaded rim.

13. The treatment device as claimed in claim 1 wherein the distal end of the introducer is provided with a beaded or rounded rim.

14. A device for treatment of a canal associated with an orifice of a human or animal body, including:

a stem portion adapted for insertion along the canal, which stem portion includes at least one fluid flow passage extending along the stem portion;

an expandable member carried by the stem portion for occlusion of an inner end region of the canal;

a cap slidably mountable on the stem portion, proximally of the expandable member and configured as a receptacle portion, open distally, for occlusion of an outer end of the canal to thereby define, with the expandable member, a treatment cavity that includes the canal and surface(s) about the outer end of the canal;

one or more orifices in the stem portion through which treatment fluid is deliverable to the treatment cavity via said at least one fluid flow passage;

a fluid reservoir incorporated into the cap, which fluid reservoir is adapted to receive and store treatment fluid for contact with said surfaces about the outer end of the canal; and an introducer for introducing the stem portion and expandable member into the body, the stem portion being slidable within and relative to the introducer, the introducer being positionable at an entrance to the canal or short thereof in a proximal direction, for introduction of the expandable member into the canal, and wherein the introducer is removable from the stem portion such that following removal, the cap is slidable relative to the stem portion with a sealing fit therebetween and movable to a distal position against the entrance to the canal.

15. The device as claimed in claim 14 wherein the introducer is removable by means of a slitted, perforable or frangible construction.

16. The device as claimed in claim 15 wherein the introducer has a lengthwise slit.

17. The device as claimed in claim 14 wherein an insertion tool is provided for pushing the cap distally.

18. The device as claimed in claim 17 wherein the insertion tool is removable by means of a slitted, perforable or frangible construction.

19. The treatment device as claimed in claim 14 wherein the distal end of the introducer is provided with a beaded or rounded rim.

20. A method of treating a cervical canal of a human or animal body, including:

inserting a stem portion along the cervical canal using an introducer positioned at the external os of the cervical canal or short thereof in a proximal direction, the stem portion being slidable within and relative to the introducer;

expanding an expandable member carried by the stem portion to occlude an inner end region of the cervical canal;

distally sliding a cap which is mounted on the stem portion proximally of the expandable member to occlude an outer end of the cervical canal to thereby define, with the expandable member, a treatment cavity that includes the canal and surface(s) about the outer end of the canal, wherein a fluid reservoir is incorporated into the cap, which fluid reservoir is adapted to receive and store treatment fluid;

delivering treatment fluid to the treatment cavity such that treatment fluid received and stored in the reservoir contacts said surface(s) about the outer end of the cervical canal, wherein the introducer is removed before the cap slides to occlude the outer end of the cervical canal or the introducer is retracted proximally prior to delivering the treatment fluid.

21. The method as claimed in claim 20 wherein the fluid reservoir includes a fluid retention element which is pre-loaded with the treatment fluid prior to distally sliding the cap and the stem portion includes at least one fluid flow passage extending therealong and treatment fluid is delivered to the treatment cavity via said at least one fluid flow passage after the cap occludes the outer end of the cervical canal.

22. The method as claimed in claim 20 wherein the method comprises removing the introducer from the stem portion, such that the cap is slidable relative to the stem portion with a sealing fit therebetween.

23. The method as claimed in claim 20 further including using an insertion tool for distally sliding the cap.

24. The method as claimed in claim 20 including repositioning the human or animal during treatment.

* * * * *